(12) United States Patent
Garofano

(10) Patent No.: US 6,495,153 B2
(45) Date of Patent: Dec. 17, 2002

(54) ANTI-FUNGAL COMPOSITION

(75) Inventor: Dona Garofano, 123 Skyline Dr., Ringwood, NJ (US) 07456

(73) Assignee: Dona Garofano, Ringwood, NJ (US)

( * ) Notice: Subject to any disclaimer, the term of this patent is extended or adjusted under 35 U.S.C. 154(b) by 0 days.

(21) Appl. No.: 09/783,908

(22) Filed: Feb. 15, 2001

(65) Prior Publication Data

US 2001/0005510 A1 Jun. 28, 2001

Related U.S. Application Data

(63) Continuation-in-part of application No. 09/190,932, filed on Nov. 12, 1998, now abandoned.
(60) Provisional application No. 60/065,301, filed on Nov. 13, 1997.

(51) Int. Cl.⁷ ............................................... A01N 25/32
(52) U.S. Cl. ..................... 424/406; 424/405; 424/407; 424/409; 424/417; 424/420; 424/421; 424/726; 424/769; 424/773
(58) Field of Search ................................. 424/405, 406, 424/407, 409, 417–421, 726, 769, 773, 725

(56) References Cited

U.S. PATENT DOCUMENTS 5,455,033 A * 10/1995 Silverman et al. ........ 424/195.1
5,869,062 A * 2/1999 Oliver ..................... 424/195.1
5,948,439 A * 9/1999 Forman et al. ............. 424/466

OTHER PUBLICATIONS

Merck Index p. 470, 471, 1968.*

Milks Practical Veterinary Pharmacology –p. 282–285, 292, 293, 1949.*

Culpepper's Complete Herbal p. 9, 10, 1995.*

* cited by examiner

Primary Examiner—Neil S. Levy
(74) Attorney, Agent, or Firm—Wendy W. Koba

(57) ABSTRACT

An anti-fungal treatment, for use on skin, comprising an anti-fungal component and a skin treating component. The skin treating component either absorbs moisture on the skin to make an undesirable environment for the fungus, or treats the skin to allow the anti-fungal component to penetrate, allow the skin to heal, and to create an unpleasant, oily environment for the fungus. The anti-fungal component is a combination of goldenseal root powder with ipe roxo powder and poke root powder. The skin treating component is either a skin softening mixture, such as D-alpha tocopherol and olive oil, or is a dehydrator, such as arrowroot and ball clay. A further combined anti-fungal and aromatic component preferably comprises lavender oil, and may also comprise teatree oil.

11 Claims, 1 Drawing Sheet

ANTI-FUNGAL COMPOSITION

CROSS REFERENCES AND RELATED SUBJECT MATTER

This application relates to subject matter contained in provisional patent application Ser. No. 60/065,301, filed in the United States Patent Office on Nov. 13, 1997.

This application is filed as a continuation-in-part of Ser. No. 09/190,932, filed Nov. 12, 1998, and hereby abandoned.

BACKGROUND OF THE INVENTION

The invention relates to an anti-fungal composition. More particularly, the invention relates to an improved topical anti-fungal composition, produced in either powder or cream form, which is comprised of and utilizes the natural anti-fungal and anti-viral properties of an unobvious combination of various herbs and vitamins.

Many people suffer from discomfort and unease caused from infections of their feet. This can prove to be quite debilitating considering the amount of time people normally spend on their feet. One of the more common infections that feet are prone to is known as Athlete's Foot. This condition often causes itching, burning and blisters between the toes. Besides being extremely uncomfortable, this infection can lead to more serious infections if not properly treated in time. Furthermore, it is quite contagious.

Many of the commercially available remedies sold in drug stores consist of a powder based substance. These remedies are typically sprinkled in one's shoes or socks and have a deodorizing effect. A major disadvantage of these formulations is the drying action of the powder upon the foot, leading to a cracking or hardening of the skin. In fact, tough dry skin can actually prevent anti-fungal agents from reaching and killing the fungus. A subsequent disadvantage of these treatments is that they,are not intended to actually cure an infection; rather, their primary purpose is to deodorize the feet.

Furthermore, anti-fungal compositions found heretofore in the prior art have utilized one or more of the anti-fungal and anti-viral herbs which comprises the composition of the instant invention. None of said prior compositions has, however, combined all of the various herbs, vitamins and oils contemplated by the instant invention. Furthermore, none of said prior compositions found in the art have been as aggressive and effective at battling and eliminating dermal fungal/viral infections.

While these compositions disclosed in the prior art may be suitable for the particular purpose employed, or for general use, they would not be as suitable for the purposes of the present invention as disclosed hereafter.

SUMMARY OF THE INVENTION

It is an object of the invention to produce an improved anti-fungal composition which effectively combats fungus, creates an environment on the skin which is hot conducive to fungus growth, and which promotes healing of the skin.

It is another object of the invention to produce an improved topical anti-fungal composition which, through the combination of various substances such as goldenseal root powder, ipe roxo powder, arrowroot, lavender oil, tea tree oil and poke root powder, attacks a dermal fungus or virus and deters the proliferation of said fungus or virus beyond the affected area.

It is a further object of the invention to produce an improved topical anti-fungal composition which can be produced in either cream or powder form.

It is a still further object of the invention to produce an improved topical anti-fungal composition in a cream form which, through the use of one or more vitamins such as d-alpha tocopherol and one or more oils such as olive oil or tea tree oil, can soften skin tissue so as to allow the antifungal components to penetrate, promote healing of the skin, and prevent the formation of scar tissue thereupon.

It is another object of the instant invention to produce an improved topical anti-fungal composition in a powder form which can be applied when application of the cream would be inconvenient, and to dehydrate the affected area so as to inhibit the growth of fungus thereat.

The invention is a anti-fungal treatment, for use on skin, comprising an anti-fungal component and a skin treating component. The skin treating component either absorbs moisture on the skin to make an undesirable environment for the fungus, or treats the skin to allow the anti-fungal component to penetrate, allow the skin to heal, and to create an unpleasant, oily environment for the fungus. The anti-fungal component is a combination of goldenseal root powder with ipe roxo powder and poke root powder. The skin treating component is either a skin softening mixture, such as D-alpha tocopherol and olive oil, or is a dehydrators such as arrow root and ball clay. A further combined anti-fungal and aromatic component preferably comprises lavender oil, and may also comprise teatree oil.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

DETAILED DESCRIPTION OF THE PREFERRED EMBODIMENTS

Figure 1:
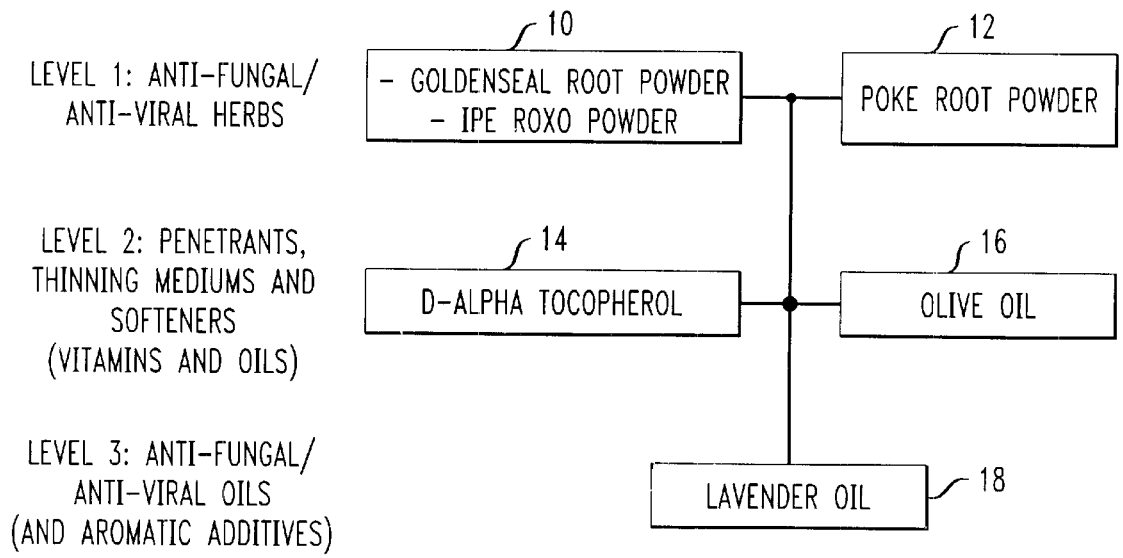
FIG. 1 is a block diagram depicting the combination of substances used to form an improved anti-fungal composition in a cream form.

FIG. 1 illustrates the combination of substances used to form an improved anti-fungal composition in a cream form. As illustrated, level-one additives comprise both known 10 and previously unknown 12 herbal anti-fungal and anti-viral ingredients. More specifically, the external medicinal anti-fungal and anti-viral effects of goldenseal root powder and ipe roxo powder are combined with poke root powder to combat existing fungus and virus affected areas and prevent new fungal/viral growth upon and about said affected area.

Level-two additives comprise penetrants, softeners and thinners which penetrate the callous, thick layer of skin tissue surrounding the affected area. More specifically, d-alpha tocopherol 14 (a natural vitamin E oil) in concentrated form is thinned by olive oil 16 (which possesses skin tissue softening properties), thus causing the level-one anti-fungal and anti-viral herbs to penetrate the effected area. Furthermore, the d-alpha tocopherol 14 prevents the formation of scar tissue upon and around the affected area.

Lavender oil 18 comprises a level-three anti-fungal/anti-viral additive as well as an aromatic additive. In addition to providing heretofore unknown anti-viral and anti-fungal characteristics, the lavender oil 18 also contributes a pleasant fragrance to the amalgam composition. The overall composition of the improved anti-fungal/anti-viral cream provides a synergistic combination of natural herbs (level-one) and vitamins and oils (levels two and three) which can halt and destroy existing fungal and viral growth, and create an environment upon the affected skin tissue area which is not conducive to future fungal and viral growth.

Figure 2:
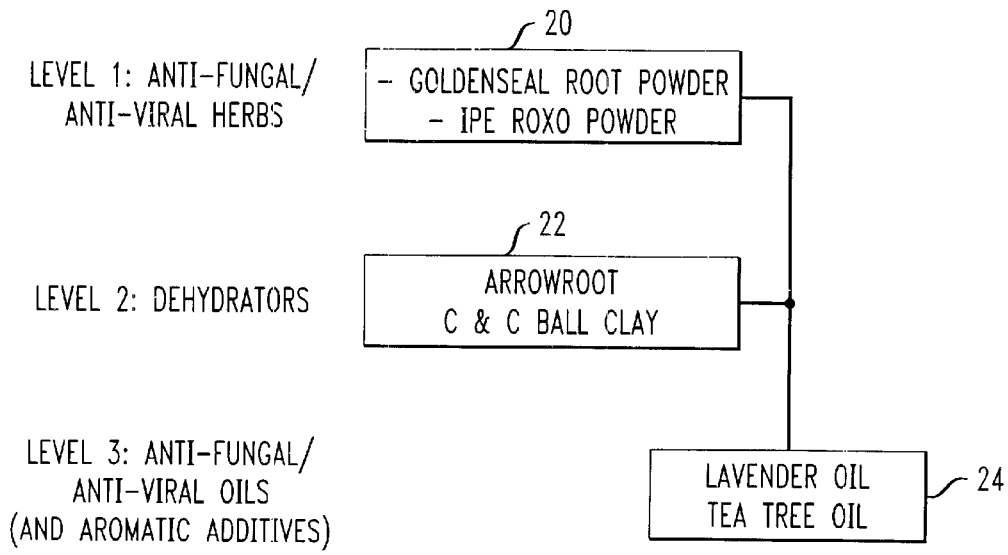
FIG. 2 is a block diagram depicting the combination of substances used to form an improved anti-fungal composition in a powder form.

FIG. 2 illustrates the combination of substances used to form an improved anti-fungal composition in a powder form. Level-one additives comprise commonly well known herbal anti-fungal and anti-viral ingredients such as goldenseal root powder and ipe roxo powder 20. As mentioned previously, these natural herbal substances combat existing fungus and virus affected areas and prevent new fungal/viral growth upon and about said affected area.

Level-two additives comprise dehydrators such as arrowroot and ball clay 22. Typically, talcum powder (i.e. sodium bicarbonate) is used as a base for most powder-form compounds. However, talcum powder is arguably toxic, and hence undesirable as an ingredient in the instant invention. Instead, the utilization of arrowroot and ball clay 22 causes dehydration of the affected area, thus removing the moist area upon which fungal and viral growth commonly thrive. In addition, the arrowroot and ball clay 22 provides the affected skin tissue area with a smooth, comfortable sensation.

Finally, the aromatic oil additives of level-three serve several purposes. Primarily, the lavender oil and tea tree oil 24 possess anti-fungal and anti-viral characteristics which were previously unknown. These oils combine with the natural anti-fungal and anti-viral herbs of level one (goldenseal root powder and ipe roxo powder 10) and enhance the characteristics thereof to effectively combat the growth and spread of existing fungal and viral growth. In addition, the lavender oil and tea tree oil 24 also help to halt the spread of fungal and viral growth by creating a hostile environment upon the affected skin tissue area. Just as fungal and viral growth cannot thrive in a dry area (hence the reason for the dehydrators of level-two), so too is such fungal and viral growth incapable of flourishing upon the oily surface created by the lavender and tea tree oil 24. Finally, the addition of the lavender and teal tree oil 24 provides a pleasant aroma similar to the utilization of said lavender oil as a level three additive in the cream form of the improved anti-fungal composition.

In accordance with the present invention, the combination of components in the manner described below function to throw the flowering fungus into spore form, which is dormant. By virtue of using the anti-fungal agent of the invention with the inclusion of the skin treatment component, the composition is able to maintain contact with the skin, allowing the body to rid itself of the fungus, since it has become dormant. The body, as it sloughs off the layers of tissue through its normal processes, takes the fungal spores with it. Over time (approximately three to nine months), normal tissue growth returns and the deteriorated skin tissue returns to health.

By keeping the fungus in spore form and allowing the body's natural cleansing process, the area of fungal infection is brought under control and eradicated. The combination and percentage of ingredients as identified in the table below are considered to be exemplary and have been successful in attacking the fungus from many different angles, preventing it from survival.

TABLE I

| INGREDIENT | POWDER (%) | CREAM (%) |
| --- | --- | --- |
| Ipe Roxo powder | 20% | 25% |
| Goldenseal root powder | 3% | 15% |
| Lavender oil | 1% | 1% |
| Ball clay | 40% | — |
| Arrowroot | 35% | — |
| Tea tree oil | 1% | 1% |
| D-alpha tocopherol | — | 11% |
| Olive oil | — | 20% |

It is to be understood that these various percentages may vary slightly and still yield a viable anti-fungal composition of the present invention. For example, in alternative cream form, the tea tree oil can be omitted and the percentage of D-alpha tocopherol increased to 12%. Various other agents, such as beeswax and aloe vera, may be added to the cream version of the composition as hardening agents, if desired.

What is claimed is:

1. An anti-fungal composition, for topical application to skin, comprising:

an anti-fungal component comprising a mixture of goldenseal root powder and ipe roxo powder;

by a skin treatment component, the skin treatment component to effectuate treatment by allowing the skin surface to remain in contact with and absorb the anti-fungal component, said skin treatment component comprises tea tree oil and either one of a powder component, comprising ball clay and arrowroot, and a cream component, comprising D-alpha tocopherol and olive oil; and lavender oil, exhibiting both anti-fungal and aromatic properties.

2. The anti-fungal composition as recited in claim 1, wherein the composition comprises a powder and further comprises tea tree oil exhibiting both anti-fungal and aromatic properties.

3. The anti-fungal composition as recited in claim 1, wherein the composition comprises a cream and the skin treatment component comprises D-alpha tocopherol.

4. The anti-fungal composition as recited in claim 3, wherein the skin treating component further comprises olive oil.

5. The anti-fungal composition as recited in claim 1, wherein the anti-fungal component further comprises poke root powder.

6. The anti-fungal composition as recited in claim 2, wherein the skin treating component is a dehydrator which comprises a mixture of arrowroot and ball clay.

7. The anti-fungal composition as recited in claim 3 wherein the ipe roxo powder comprises approximately 25% of the cream composition, the goldenseal root powder comprises approximately 15% of the cream composition, and the lavender oil comprises approximately 1% of the cream composition.

8. The anti-fungal composition as defined in claim 7 wherein the D-alpha tocopherol comprises approximately 11% of the cream composition.

9. The anti-fungal composition as defined in claim 4 wherein the olive oil comprises approximately 20% of the cream composition.

10. The anti-fungal composition as defined in claim 2 wherein the ipe roxo powder comprises approximately 20% of the powder composition, the goldenseal root powder comprises approximately 3% of the powder composition, and the lavender oil comprises approximately 1% of the powder composition.

11. The anti-fungal composition as defined in claim 6 wherein the ball clay comprises approximately 40% of the powder composition and the arrowroot comprises approximately 35% of the powder composition.

* * * * *